(12) United States Patent
Kleczewski et al.

(10) Patent No.: US 9,651,426 B2
(45) Date of Patent: May 16, 2017

(54) LIGHT SOURCE WITH CONTROLLABLE LINEAR POLARIZATION

(71) Applicant: Agilent Technologies, Inc., Santa Clara, CA (US)

(72) Inventors: Adam Kleczewski, San Francisco, CA (US); Richard P Tella, Sunnyvale, CA (US); Dower Cameron Bricker, Selby (AU); Yang Han, Sunnyvale, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 14/788,534

(22) Filed: Jun. 30, 2015

(65) Prior Publication Data

US 2017/0003170 A1    Jan. 5, 2017

(51) Int. Cl.
| | |
|---|---|
| *G01J 4/02* | (2006.01) |
| *H01S 5/34* | (2006.01) |
| *H01S 5/00* | (2006.01) |
| *H01S 5/40* | (2006.01) |
| *G02B 5/30* | (2006.01) |
| *G02B 27/28* | (2006.01) |
| *G02B 26/00* | (2006.01) |

(52) U.S. Cl.
CPC .............. *G01J 4/02* (2013.01); *G02B 5/3058* (2013.01); *G02B 26/00* (2013.01); *G02B 27/286* (2013.01); *H01S 5/0071* (2013.01); *H01S 5/3401* (2013.01); *H01S 5/4012* (2013.01); *H01S 5/4075* (2013.01)

(58) Field of Classification Search
CPC ......... G01J 4/04; G01N 21/21; G01N 21/211; G01N 21/19; G01N 21/6445
USPC ......................................................... 356/368
See application file for complete search history.

(56) References Cited

U.S. PATENT DOCUMENTS

| | | | |
|---|---|---|---|
| 4,512,638 A | 4/1985 | Sriram | |
| 6,075,235 A * | 6/2000 | Chun | ........................ G01J 4/04 250/208.1 |
| 8,913,800 B2 | 12/2014 | Rowe | |
| 9,188,874 B1 * | 11/2015 | Johnson | ............... G02B 21/002 |

(Continued)

FOREIGN PATENT DOCUMENTS

WO    2013/101252 A1    7/2013

OTHER PUBLICATIONS

Extended European Search Report dated Dec. 12, 2016, EP application 16181685.5.

*Primary Examiner* — Tarifur Chowdhury
*Assistant Examiner* — Md M Rahman

(57) ABSTRACT

A light source having first and second wire-grid polarizers and a laser that emits a beam of linearly polarized light that is characterized by a propagation direction is disclosed. The first wire-grid polarization filter is characterized by a first linear polarization pass direction and a first actuator for causing the first linear polarization pass direction to rotate relative to the beam of linearly polarized light. The second wire-grid polarization filter is characterized by a second linear polarization pass direction and a second actuator for causing the second linear polarization pass direction to rotate relative to the beam of linearly polarized light. A controller sets the first and second linear polarization pass directions to provide linearly polarized light having a specified polarization direction.

12 Claims, 3 Drawing Sheets

(56) References Cited

U.S. PATENT DOCUMENTS

| | | | |
|---|---|---|---|
| 2002/0159011 A1* | 10/2002 | Ikeno | G02F 1/133555 |
| | | | 349/117 |
| 2011/0080311 A1 | 4/2011 | Pushkarsky | |
| 2013/0026368 A1* | 1/2013 | Herzinger | G01J 4/04 |
| | | | 250/341.3 |
| 2013/0137961 A1 | 5/2013 | Barnes | |
| 2015/0034612 A1* | 2/2015 | Hosseini | B23K 26/0069 |
| | | | 219/121.61 |
| 2015/0172631 A1* | 6/2015 | Kasahara | H04N 5/3572 |
| | | | 348/46 |
| 2015/0276391 A1* | 10/2015 | Murase | G01B 11/26 |
| | | | 356/138 |

* cited by examiner

LIGHT SOURCE WITH CONTROLLABLE LINEAR POLARIZATION

BACKGROUND

Quantum cascade lasers provide a tunable mid-infrared (MIR) light source that can be used for spectroscopic measurements and images. Many chemical components of interest have molecular vibrations that are excited in the MIR region of the optical spectrum, which spans wavelengths between 5 to 25 microns. Hence, measuring the absorption of MIR light or reflection of MIR light at various locations on a sample can provide useful information about the chemistry of the sample as a function of position on the sample.

SUMMARY

The present invention includes a light source having first and second wire-grid polarizers and a laser that emits a beam of linearly polarized light that is characterized by a propagation direction. The first wire-grid polarization filter is characterized by a first linear polarization pass direction and a first actuator for causing the first linear polarization pass direction to rotate relative to the beam of linearly polarized light. The first wire-grid polarization filter is positioned such that the beam of linearly polarized light passes through the first wire-grid polarization filter. The second wire-grid polarization filter is characterized by a second linear polarization pass direction and a second actuator for causing the second linear polarization pass direction to rotate relative to the beam of linearly polarized light. The second wire-grid polarization filter is positioned such that the beam of linearly polarized light passes through the second wire-grid polarization filter after passing through the first wire-grid polarization filter. A controller sets the first and second linear polarization pass directions to provide linearly polarized light having a specified polarization direction.

In one aspect of the invention, the first wire-grid polarization filter includes a parallel grid of metallic lines on a first transparent planar substrate, the first transparent planar substrate being angled relative to the propagation direction such that light reflected from the first wire-grid polarization filter does not propagate in a direction parallel to the propagation direction.

In another aspect of the invention the second wire-grid polarization filter includes a parallel grid of metallic lines on a second transparent planar substrate, the second transparent planar substrate is angled relative to the propagation direction such that light reflected from the second wire-grid polarization filter does not propagate in a direction parallel to the propagation direction and such that light reflected from the second wire-grid polarization filter does not propagate in a direction parallel to light reflected from the first wire-grid filter.

In another aspect of the invention, the first laser is a quantum cascade laser that emits light in a band of wavelengths between 2 and 14 microns.

In another aspect of the invention, the first and second planar substrates are transparent to light of wavelengths between 2 and 14 microns. The first planar substrate can be a glass that includes a substance chosen from the group consisting of $BaF_2$, ZnSe, ZnS, ZnTe, diamond, and Si.

In a further aspect of the invention, the light source includes a second laser and a beam director. The second laser emits a beam of linearly polarized light in a different band of wavelengths than the first laser. The beam director causes light from the second laser to enter the first wire-grid polarization filter on a path that is coincident with a path that light from the first laser follows through the first wire-grid polarization filter.

In yet another aspect of the invention, the light source includes first and second optical assemblies. The first optical assembly directs light leaving the second wire-grid polarization filter onto a specimen. The second optical assembly collects light leaving the specimen and directs the collected light to a polarization analyzer that measures an intensity of light as a function of a polarization direction. The controller causes the polarization analyzer to measure the intensity of light for a plurality of different first and second linear polarization pass directions.

DETAILED DESCRIPTION

Figure 1:
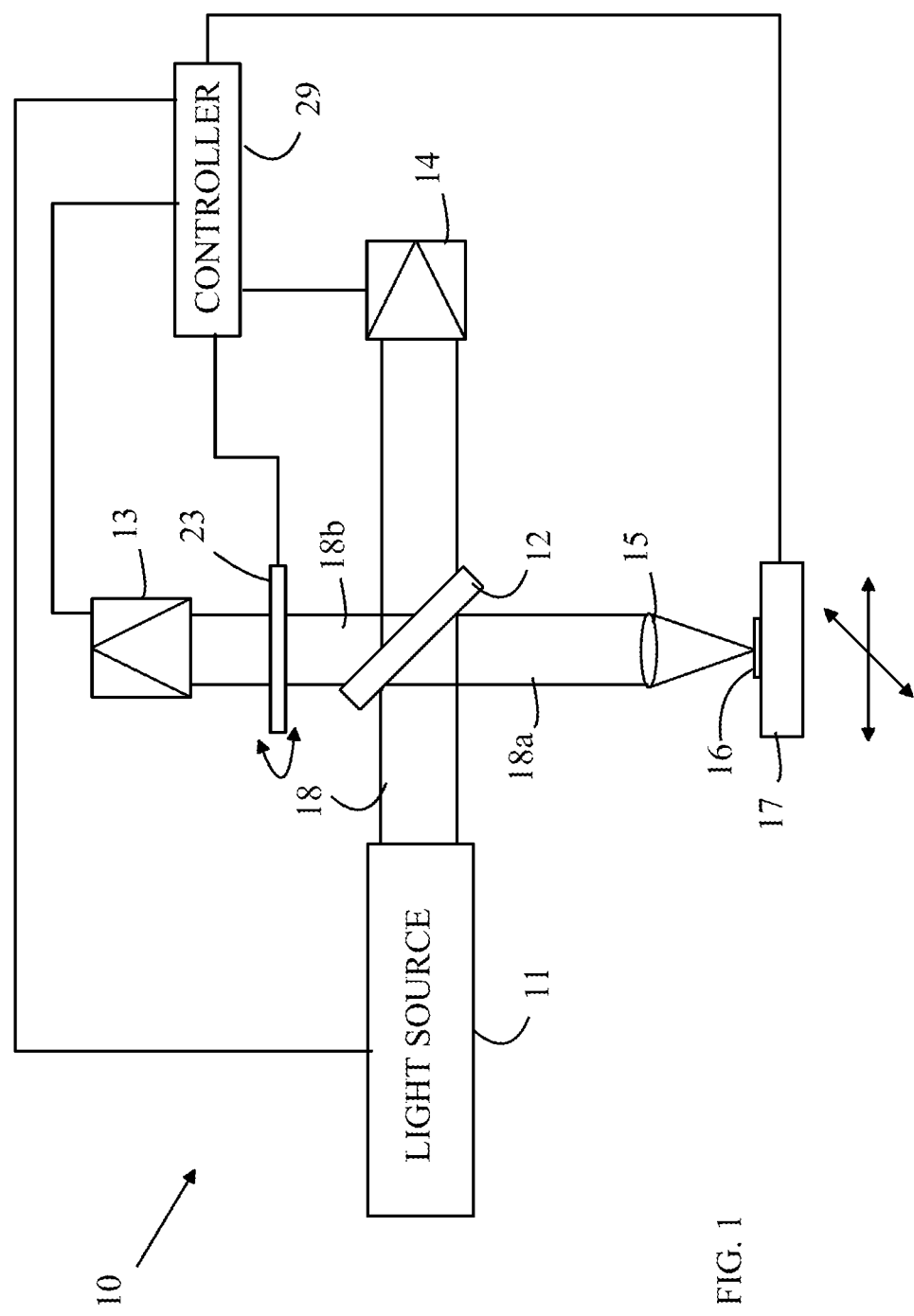
FIG. 1 illustrates one embodiment of a spectrometer that uses a light source according to the present invention.

Imaging systems based on MIR light sources can provide information about the underlying chemical nature of the sample being imaged. In addition, by measuring the reflection or absorption of the incident MIR light as a function of wavelength, more precise identification of the chemical nature of the sample at the point at which the data is being taken can be obtained.

In absorption spectroscopy, the sample is illuminated with light and the amount of light that is reflected from the sample is measured. The process is repeated for a number of wavelengths of the light to generate a spectrum consisting of the intensity of the reflected light as a function of wavelength. The fraction of the incoming light that is reflected from the sample is related to the intensity of the light that was absorbed by the sample. Absorption spectra can be used to identify the chemical compounds in the sample. Hence, an image of a sample in which each pixel of the image includes an absorption or reflection spectrum as a function of wavelength is useful in visualizing the distribution of different chemical compounds in the sample.

The light that is reflected from a specimen depends on the nature of the surface of the specimen. In general, the reflected light is a mixture of specular reflected light from flat surfaces such as the facets of crystals in the sample and diffuse reflected light reflected from rough surfaces or powders. The spectra generated by specularly reflected light differ from those generated by diffusely reflected light. Since many specimens of interest generate a compound spectrum with an unknown ratio of the two types of reflections, interpreting the images in terms of the chemical composition of a sample as a function of position on the sample presents significant challenges. These challenges can be significantly reduced if the contribution of each type of reflection to the measured spectrum at each point in the specimen can be separated.

The present invention is based on the observation that polarized light that is undergoing specular reflection remains polarized. In contrast, diffusely reflected polarized light is depolarized. Hence, the diffusely reflected light can be selectively measured with the aid of a linear polarization filter. If the incident laser light is linearly polarized, the specularly reflected light will be linearly or elliptically polarized. The elliptically polarized light can be characterized by two linear polarizations that are orthogonal to one another as measured on a coordinate system that is fixed relative to the specimen. A linear polarization filter blocks linearly polarized light that has a direction of polarization that is orthogonal to a polarization axis defined on the filter. If a light beam is linearly polarized with a direction that is parallel to that axis, all of the light passes through the filter. If the light beam is linearly polarized along a direction that is orthogonal to that axis, all of the light is blocked. In general, if the light is linearly polarized along an axis that is at an angle of θ with respect to the polarization axis, the light can be viewed as having a component that is parallel to the polarizer axis and one that is orthogonal to the polarizer axis. The parallel component passes through the filter and the orthogonal component is blocked by the filter. Hence, for an elliptically polarized beam having linearly polarized components $I_s$ and $I_d$ relative to the coordinate system on the sample, part of the light in each component will pass through the filter. The amount of light will depend on the angle between the polarization axis on the filter and the polarization of each linearly polarized component. By making a number of measurements at different relative angles between the polarization axis and the coordinate system on the sample, different combinations of the diffuse and specular light intensity, $I_d$, $I_s$ and $I_p$ can be measured. In addition, measurements in which the direction of polarization of the incoming light on the sample are needed to provide other combinations of the diffuse and specular light intensities. These measurements can then be combined to obtain the diffuse and specular components.

Refer now to FIG. 1, which illustrates one embodiment of a spectrometer that uses a light source according to the present invention. Imaging system 10 includes a light source 11 that generates a collimated light beam 18 having a narrow band of wavelengths in the MIR. In one aspect of the invention, light source 11 includes a quantum cascade laser having a tunable wavelength that is under the control of a controller 29. Light source 11 generates a linearly polarized beam of light whose polarization direction is also under the control of controller 29. The manner in which the polarization direction of the light leaving light source 11 is set will be discussed in detail below.

Collimated light beam 18 is split into two beams by a partially reflecting mirror 12. Light beam 18a is directed to a first optical assembly that directs the light in that beam onto a specimen 16. In particular, lens 15 focuses that beam onto a specimen 16 that is mounted on xy-stage 17 that can position specimen 16 relative to the focal point of lens 15. Light that is reflected back from specimen 16 is collected by a second optical assembly and directed to a polarization analyzer. In particular, the light leaving specimen 16 is collimated into a second beam that has a diameter determined by the aperture of lens 15 and returns to partially reflecting mirror 12 along the same path as light beam 18a. While the first and second beams are shown as having the same cross-section in FIG. 1, it is to be understood that the second beam could have a different cross-section than the first beam. A portion of the second beam is transmitted through partially reflecting mirror 12 and impinges on a first light detector 13 as shown at 18b. Light detector 13 generates a signal related to the intensity of light in beam 18b. Controller 29 computes an image as a function of position on specimen 16 by moving specimen 16 relative to the focal point of lens 15 using xy-stage 17.

Controller 29 also monitors the beam intensity of the light in collimated light beam 18 using a second light detector 14 that receives a portion of the light generated by light source 11 through partially reflecting mirror 12. Light source 11 is typically a pulsed source. The intensity of light from pulse to pulse can vary significantly, and hence, the pixels of the image are corrected for the variation in intensity by dividing the intensity measured by light detector 13 by the intensity measured by light detector 14. In addition, since the light intensity from light source 11 is zero between pulses, controller 29 only sums the ratio of intensities from light detectors 13 and 14 during those times at which the output of light detector 14 is greater than some predetermined threshold. This aspect of the present invention improves the signal-to-noise ratio of the resultant image, since measurements between pulses contribute only noise, which is removed by not using measurements between pulses.

Imaging system 10 utilizes a linear polarization filter 23 which is under the control of controller 29 to separate the specularly reflected light from the diffusely reflected light. Linear polarization filter 23 is rotated through a number of angles. For each (x,y) coordinate of xy-stage 17 and wavelength of light from light source 11, controller 29 measures the intensity of light reflected back from specimen 16 as a function of the angle of rotation of the polarization axis of linear polarization filter 23. In one aspect of the invention, the intensity measured by light detector 13 is normalized to the output of light detector 14 to correct for variations in the intensity of light generated by light source 11.

In addition, the polarization direction of the light from light source 11 is changed and the output of light detector 13 is again measured for a plurality of angles of linear polarization filter 23. Hence, a complete set of measurements at any given wavelength of light from light source 11 includes the intensity of light detected by light detectors 13 and 14 for a plurality of different angles of linear polarization filter 23 and a plurality of different polarization directions of the light from light source 11. The measured values are then fitted to a function to determine the intensities of the specularly reflected light and the diffusely reflected light. The details of this fitting process are discussed in a co-pending U.S. patent application Ser. No. 14/683,841, filed Apr. 10, 2015, which is hereby incorporated by reference, and will not be discussed in detail here, as the present application is directed to improved embodiments of light source 11.

Figure 2:
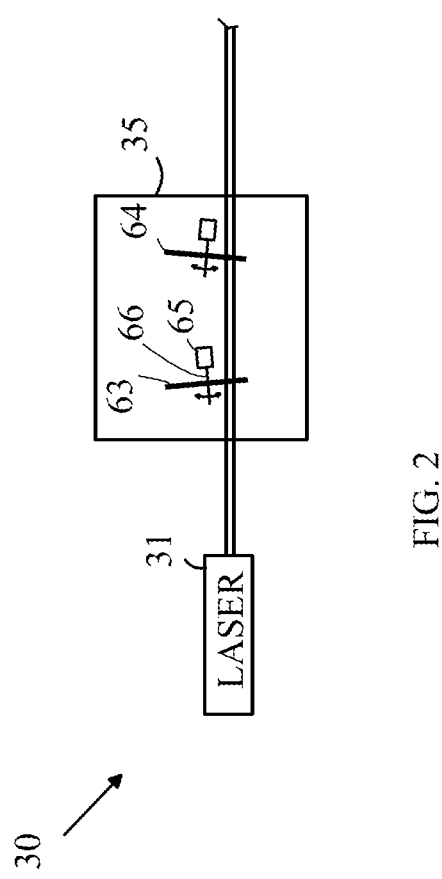
FIG. 2 illustrates one embodiment of a light source according to the present invention.

Light source 11 must operate over a wide range of wavelengths and intensities and provide a plurality of different output linear polarization angles. Refer now to FIG. 2, which illustrates one embodiment of a light source according to the present invention. Light source 30 includes a quantum cascade laser 31 and a polarization rotator 35 that sets the output beam polarization direction. To simplify the following discussion, a polarization filter that passes light having a particular linear polarization while reflecting or absorbing light having other linear polarizations will be referred to as a polarizer.

Polarization rotator 35 includes first and second wire-grid polarizers 63 and 64, respectively. Each wire-grid polarizer has a pattern of parallel metallic lines disposed on a substrate that is transparent to the wavelength of light of the linearly polarized light. Linearly polarized light that is properly aligned with the direction of the metallic lines is transmitted through the polarizer. Light with different linear polarizations is reflected. The angle of the line pattern relative to the light leaving quantum cascade laser 31 is set by an actuator the causes the wire-grid polarizer to rotate about a shaft. An exemplary actuator and a shaft are labeled at 65 and 66, respectively. To simplify the drawing, the control wiring to quantum cascade laser 31 and the wire-grid polarizers have been omitted from the drawing.

In one aspect of the invention, the angle of the plane of the substrate relative to the beam direction of quantum cascade laser 31 is different from 90 degrees to prevent light reflected from the wire-grid polarizers from entering the optical chain. In one exemplary embodiment, the plane of the substrates is set at an angle between 3 and 6 degrees. However, other angles could be utilized. If the angle is too great, the size of the wire-grid polarizers must be increased. Since the substrates must be made from a material that is transparent to MIR light over wide range of wavelengths, cost considerations favor smaller angles.

Quantum cascade lasers generate linearly polarized light. To provide light of any desired linear polarization direction, at least two wire-grid polarizers must be utilized. For the purpose of this discussion, it will be assumed that the polarization direction of the light leaving quantum cascade laser 31 is 0 degrees. Assume that a polarization of 90 degrees is desired. A single polarizer with the pass direction set to 90 degrees will not pass any light, since the input beam has no polarization component at 90 degrees. Hence, the first wire grid polarizer is set to pass light having a polarization angle of 45 degrees. The incident light has one component parallel to this direction with an intensity that is reduced by a factor 2. The second polarizer is then set to pass light at 90 degrees to the original beam polarization direction which is an angle of 45 degrees relative to the light leaving the first polarizer. Hence, the light leaving polarization rotator 35 will be reduced in amplitude by a factor of 4.

In general, the second polarizer is set to pass light of the desired polarization direction. The first polarizer must be set to an angle that is not orthogonal to the linear polarization direction of the laser. The first polarizer can be used to set the desired light attenuation by choosing a pass angle that provides an attenuation that, when combined with the attenuation introduced by the second polarizer, provides the desired overall attenuation.

In principle, other forms of polarization rotators could be utilized. However, the conventional polarization rotators that utilize dichroism are very sensitive to the wavelength of the light being rotated. Hence, providing a polarization rotator that operates over a large range of wavelengths presents significant challenges. For example, the intensity of the rotated light changes significantly with wavelength.

In the above embodiments, the light source uses a single quantum cascade laser. While quantum cascade lasers can be tuned over a significant range of wavelengths, the range available from a single quantum cascade laser is not sufficient for many MIR imaging and spectrographic applications. In many applications, a tuning range of 5 to 14 microns is required. This tuning range can be provided by four quantum cascade lasers that each operate over a different portion of this range. It should be noted that IR transmissive glass made from $BaF_2$ or ZnSe is transparent over this entire range, and hence, a single set of wire-grid polarizers can be used over the entire range. In addition, there are other materials that are also transparent/partially transparent for this range, such as ZnS, diamond, Si or Ge windows.

Figure 3:
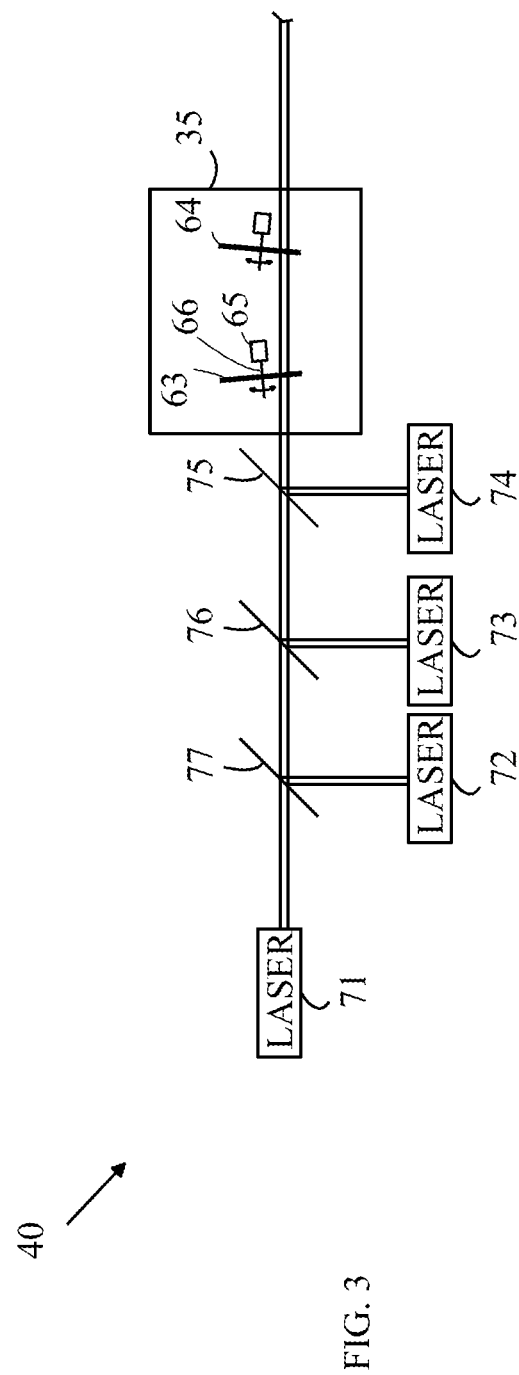
FIG. 3 illustrates a light source that utilizes multiple quantum cascade lasers and a single polarization rotator to provide polarized light of the desired wavelength and polarization direction.

Refer now to FIG. 3, which illustrates a light source that utilizes multiple quantum cascade lasers and a single polarization rotator to provide polarized light of the desired wavelength and polarization direction. Again, to simplify the drawing, the control leads to the individual quantum cascade lasers and the actuators in polarization rotator 35 have been omitted. In light source 40, the light from the individual quantum cascade lasers 71-74 is directed to the same input optical path by partially reflecting mirrors 75-77. In the simplest mode of operation, only one quantum cascade laser is active at any given time. The reflectivities of partially reflecting mirrors 75-77 are set such that the light intensity reaching polarization rotator 35 is the same for each quantum cascade laser.

In one mode of operation, a quantum cascade laser is typically pulsed at some predetermined pulse rate. By using different pulse rates for different quantum cascade lasers, the light from the different quantum cascade lasers can be detected separately, and hence, measurements can be made at multiple wavelengths at the same time. In this regard, it should be noted that polarization rotator 35 has the same settings for the wire-grid polarizers independent of the wavelength of the incident light. Hence, if two quantum cascade lasers are simultaneously providing light, the light from each quantum cascade laser will have the same linear polarization direction. Referring again to FIG. 1, the contribution of each wavelength to the light reflected from specimen 16 can be ascertained by measuring the intensity of light at light detectors 13 and 14 separately at each frequency. Hence, in addition to extending the range of the wavelengths of the incident light, the use of multiple lasers can reduce the time needed to generate a spectrum of a sample at one point on the sample by measuring the reflectivity of the sample at multiple wavelengths.

The above-described embodiments have utilized an imaging system as the exemplary system in which a light source according to the present invention operates. However, it will be apparent from the foregoing discussion that a light source according to the present invention can provide advantages in other systems in which MIR light having a controllable linear polarization is required.

The above-described embodiments of the present invention have been provided to illustrate various aspects of the invention. However, it is to be understood that different aspects of the present invention that are shown in different specific embodiments can be combined to provide other embodiments of the present invention. In addition, various modifications to the present invention will become apparent from the foregoing description and accompanying drawings. Accordingly, the present invention is to be limited solely by the scope of the following claims.

What is claimed is:

1. A light source comprising:
   a first laser that emits a beam of linearly polarized light that is characterized by a propagation direction;
   a first wire-grid polarization filter characterized by a first linear polarization pass direction and a first actuator for causing said first linear polarization pass direction to rotate relative to said beam of linearly polarized light, said first wire-grid polarization filter being positioned such that said beam of linearly polarized light passes through said first wire-grid polarization filter;
   a second wire-grid polarization filter characterized by a second linear polarization pass direction and a second actuator for causing said second linear polarization pass direction to rotate relative to said beam of linearly polarized light, said second wire-grid polarization filter being positioned such that said beam of linearly polarized light passes through said second wire-grid polarization filter after passing through said first wire-grid polarization filter; and a controller for setting said first and second linear polarization pass directions to provide linearly polarized light having a specified polarization direction, said first linear polarization pass direction being different from said second linear polarization pass direction for at least one value of said specified polarization value.

2. The light source of claim 1 wherein said first wire-grid polarization filter comprises a parallel grid of metallic lines on a first transparent planar substrate, said first transparent planar substrate being angled at an angle between 3 and 6 degrees relative to a normal to said propagation direction such that light reflected from said first wire-grid polarization filter does not propagate in a direction parallel to said propagation direction.

3. The light source of claim 2 wherein said second wire-grid polarization filter comprises a parallel grid of metallic lines on a second transparent planar substrate, said second transparent planar substrate being angled at an angle between −3 and −6 degrees relative to a normal to said propagation direction such that light reflected from said second wire-grid polarization filter does not propagate in a direction parallel to said propagation direction and such that light reflected from said second wire-grid polarization filter does not propagate in a direction parallel to light reflected from said first wire-grid polarization filter.

4. The light source of claim 2 wherein said first transparent planar substrate is a glass comprising a substance chosen from the group consisting of $BaF_2$, ZnSe, ZnS, ZnTe, diamond, and Si.

5. The light source of claim 1 wherein said first laser is a quantum cascade laser that emits light in a band of wavelengths between 2 and 14 microns.

6. The light source of claim 5 wherein said first and second planar substrates are transparent to light of wavelengths between 2 and 14 microns.

7. The light source of claim 1 further comprising
a second laser that emits a beam of linearly polarized light, said second laser emitting light in a different band of wavelengths than said first laser; and
a beam director that causes light from said second laser to enter said first wire-grid polarization filter on a path that is coincident with a path that light from said first laser follows through said first wire-grid polarization filter.

8. The light source of claim 1 further comprising:
a first optical assembly that directs light leaving said second wire-grid polarization filter onto a specimen; and
a second optical assembly that collects light leaving said specimen and directs said collected light to a polarization analyzer that measures an intensity of light as a function of a polarization direction, said controller causing said polarization analyzer to measure said intensity of light for a plurality of different first and second linear polarization pass directions, said first linear polarization pass direction being different from said second linear polarization pass direction for at least one value of said specified polarization value.

9. A method for illuminating a specimen comprising:
illuminating a first wire-grid polarization filter with a first laser that emits a beam of linearly polarized light that is characterized by a propagation direction, said first wire-grid polarization filter characterized by a first linear polarization pass direction; said first wire-grid polarization filter being positioned such that a portion of said beam of linearly polarized light passes through said first wire-grid polarization filter;
illuminating a second wire-grid polarization filter characterized by a second linear polarization pass direction, said second wire-grid polarization filter being positioned such that said beam of linearly polarized light passes through said second wire-grid polarization filter after passing through said first wire-grid polarization filter, said first and second linear polarization pass directions are adjusted such that light leaving said second wire-grid polarization filter is linearly polarized light having a specified polarization direction and amplitude, a first portion of said light leaving said second wire-grid polarization filter being directed onto said specimen and a second portion of said light leaving said second wire-grid polarization filter being directed to a detector that measures an intensity of light in said second portion.

10. The method of claim 9 wherein said first wire-grid polarization filter comprises a parallel grid of metallic lines on a first transparent planar substrate, said first transparent planar substrate being angled at an angle between 3 and 6 degrees relative to a normal to said propagation direction such that light reflected from said first wire-grid polarization filter does not propagate in a direction parallel to said propagation direction.

11. The method of claim 10 wherein said second wire-grid polarization filter comprises a parallel grid of metallic lines on a second transparent planar substrate, said second transparent planar substrate being angled at an angle between −3 and −6 degrees relative to a normal to said propagation direction such that light reflected from said second wire-grid polarization filter does not propagate in a direction parallel to said propagation direction and such that light reflected from said second wire-grid polarization filter does not propagate in a direction parallel to light reflected from said first wire-grid polarization filter.

12. The method of claim 11 further comprising collecting light leaving said specimen and directing said collected light to a polarization analyzer that measures an intensity of light as a function of a polarization direction for a plurality of different first and second linear polarization pass directions.

* * * * *